United States Patent
Hagh Gooie et al.

(10) Patent No.: US 12,409,325 B2
(45) Date of Patent: Sep. 9, 2025

(54) CLOSED-LOOP AUTOCALIBRATION METHOD FOR A COMPUTER BRAIN INTERFACE DEVICE, COMPUTER PROGRAM AND COMPUTER BRAIN INTERFACE DEVICE

(71) Applicant: CEREGATE GMBH, Munich (DE)

(72) Inventors: Saman Hagh Gooie, Hamburg (DE); Bálint Várkuti, Munich (DE); Ricardo Smits Serena, Munich (DE)

(73) Assignee: Ceregate GmbH, Munich (DE)

( * ) Notice: Subject to any disclaimer, the term of this patent is extended or adjusted under 35 U.S.C. 154(b) by 817 days.

(21) Appl. No.: 17/667,009

(22) Filed: Feb. 8, 2022

(65) Prior Publication Data
US 2022/0323767 A1 Oct. 13, 2022

Related U.S. Application Data

(63) Continuation-in-part of application No. 17/224,953, filed on Apr. 7, 2021, now Pat. No. 12,214,202.

(30) Foreign Application Priority Data

Jan. 13, 2022 (EP) .................................... 22151438

(51) Int. Cl.
*A61N 1/36* (2006.01)
*A61N 1/372* (2006.01)

(52) U.S. Cl.
CPC ..... *A61N 1/36171* (2013.01); *A61N 1/36135* (2013.01); *A61N 1/36178* (2013.01); *A61N 1/37247* (2013.01)

(58) Field of Classification Search
CPC ............... A61N 1/0534; A61N 1/0551; A61N 1/36057; A61N 1/36062; A61N 1/36082;
(Continued)

(56) References Cited

U.S. PATENT DOCUMENTS

| 4,445,512 A | 5/1984 | Krupka et al. |
| 4,488,555 A | 12/1984 | Imran |

(Continued)

FOREIGN PATENT DOCUMENTS

| DE | 102019202666 A1 | 8/2020 |
| DE | 102019209096 A1 | 12/2020 |

(Continued)

OTHER PUBLICATIONS

Anderson D.N., et al., "Optimized Programming Algorithm for Cylindrical and Directional Deep Brain Stimulation Electrodes," Journal of Neural Engineering, IOP Publishing Limited, Jan. 24, 2018, 19 pages, URL: https://doi.org/10.1088/1741-2552/aaa14b.

(Continued)

*Primary Examiner* — Amanda K Hulbert
(74) *Attorney, Agent, or Firm* — Kowert, Hood, Munyon, Rankin & Goetze, P.C.; Jeffrey C. Hood; Luke Langsjoen

(57) ABSTRACT

A computer brain interface (CBI) device of an individual applies a burst sequence of stimulation pulses to afferent sensory nerve fibers to elicit a bioelectric response via a neurostimulation interface operably connected to or integrated with the CBI device. The neurostimulation interface senses the bioelectric responses of the stimulated afferent sensory nerve fibers. The CBI device derives, based on the sensed bioelectric responses, a neural excitability profile characterizing a non-linear, dynamic excitation behavior of the afferent sensory neurons corresponding to the applied sequence of stimulation pulses. At least one stimulation parameter of the current set of stimulation parameters is adjusted based on the derived excitability profile to obtain an updated set of stimulation parameters.

20 Claims, 7 Drawing Sheets

Figure 1:
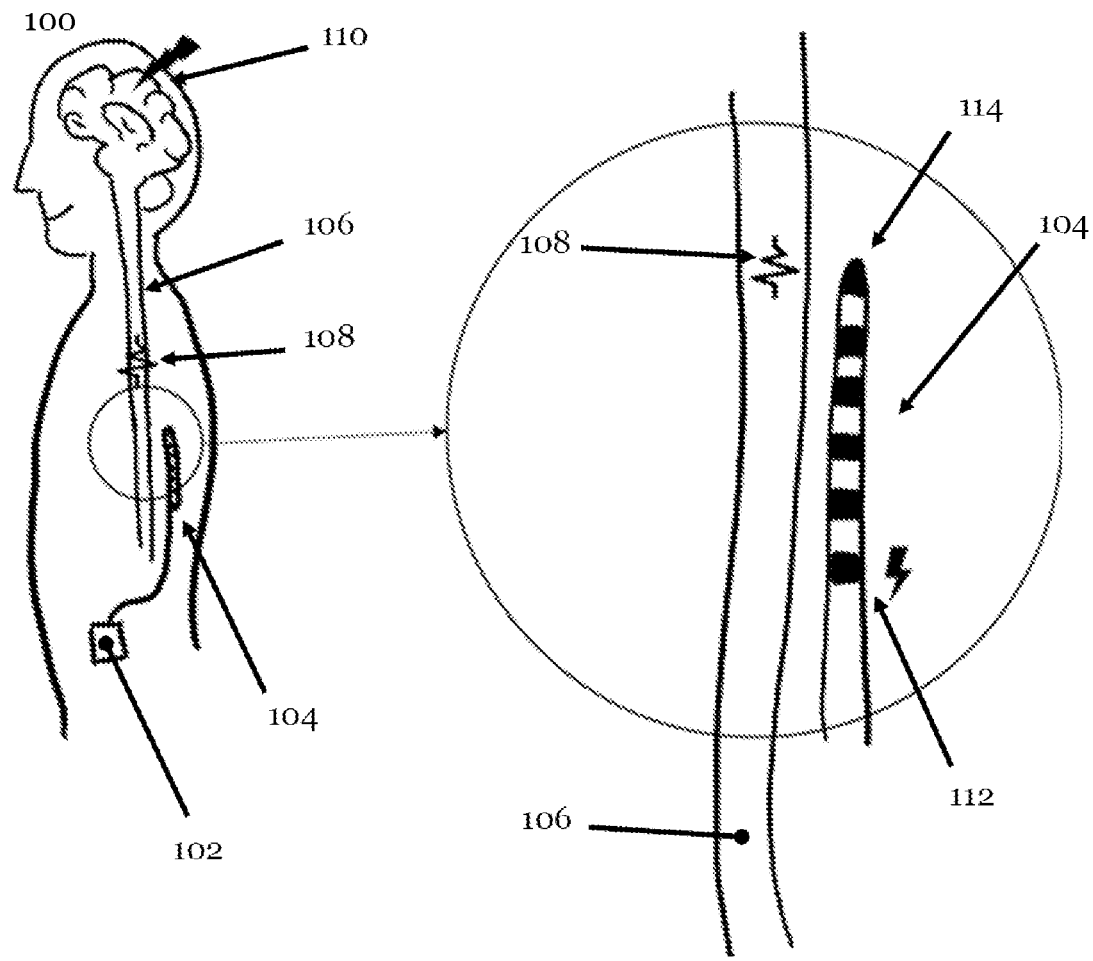

(58) Field of Classification Search
CPC .............. A61N 1/36139; A61N 1/3615; A61N 1/36167; A61N 1/36171; A61N 1/36178; A61N 1/37247; A61N 1/36003; A61N 1/36132; A61N 1/36175; A61N 1/37241; A61N 1/3606; A61N 1/36135; A61N 1/36185; G06F 3/015

See application file for complete search history.

(56) References Cited

U.S. PATENT DOCUMENTS

| | | |
|---|---|---|
| 7,751,884 B2 | 7/2010 | Ternes et al. |
| 7,774,056 B2 | 8/2010 | Torgerson |
| 8,193,766 B2 | 6/2012 | Rondoni et al. |
| 8,290,596 B2 | 10/2012 | Wei et al. |
| 8,352,029 B2 | 1/2013 | Ternes et al. |
| 8,364,271 B2 | 1/2013 | De Ridder |
| 8,380,314 B2 | 2/2013 | Panken et al. |
| 8,423,145 B2 | 4/2013 | Pless et al. |
| 8,475,172 B2 | 7/2013 | Lieberman et al. |
| 8,494,633 B2 | 7/2013 | Tobacman |
| 8,509,904 B2 | 8/2013 | Rickert et al. |
| 8,812,128 B2 | 8/2014 | Kothandaraman |
| 9,095,314 B2 | 8/2015 | Osorio et al. |
| 9,357,938 B2 | 6/2016 | Ang et al. |
| 9,636,497 B2 | 5/2017 | Bradley et al. |
| 9,713,720 B2 | 7/2017 | Zhu |
| 9,974,478 B1 | 5/2018 | Brokaw et al. |
| 10,568,559 B2 | 2/2020 | Parker et al. |
| 2003/0065366 A1 | 4/2003 | Merritt et al. |
| 2006/0129205 A1 | 6/2006 | Boveja et al. |
| 2006/0241717 A1 | 10/2006 | Whitehurst et al. |
| 2006/0241718 A1 | 10/2006 | Tyler et al. |
| 2007/0027397 A1 | 2/2007 | Fischell et al. |
| 2007/0250134 A1 | 10/2007 | Miesel et al. |
| 2008/0129517 A1 | 6/2008 | Crosby et al. |
| 2008/0139954 A1 | 6/2008 | Day et al. |
| 2009/0306741 A1 | 12/2009 | Hogle et al. |
| 2010/0057161 A1 | 3/2010 | Machado et al. |
| 2010/0063411 A1 | 3/2010 | Donoghue et al. |
| 2013/0150914 A1 | 6/2013 | Kelly et al. |
| 2013/0253299 A1 | 9/2013 | Weber et al. |
| 2014/0081348 A1 | 3/2014 | Fischell |
| 2014/0379046 A1 | 12/2014 | Tcheng et al. |
| 2015/0018724 A1 | 1/2015 | Hsu et al. |
| 2015/0073492 A1 | 3/2015 | Kilgard et al. |
| 2015/0290453 A1 | 10/2015 | Tyler et al. |
| 2016/0022992 A1 | 1/2016 | Franke et al. |
| 2016/0121118 A1 | 5/2016 | Franke et al. |
| 2017/0080226 A1 | 3/2017 | Akhoun |
| 2018/0050198 A1 | 2/2018 | Mazanec et al. |
| 2018/0229046 A1 | 8/2018 | Parker et al. |
| 2019/0030338 A1 | 1/2019 | Wu et al. |
| 2020/0269049 A1 | 8/2020 | Varkuti |
| 2020/0376272 A1* | 12/2020 | Block ................ A61N 1/36071 |

FOREIGN PATENT DOCUMENTS

| | | |
|---|---|---|
| EP | 2552304 B1 | 9/2015 |
| EP | 3229893 A1 | 10/2017 |
| EP | 3431138 A1 | 1/2019 |
| EP | 2486897 B1 | 5/2019 |
| KR | 20170132055 A | 12/2017 |
| KR | 101841625 B1 | 5/2018 |
| WO | 2012003451 A2 | 1/2012 |
| WO | 2016116397 A1 | 7/2016 |
| WO | 2018057667 A1 | 3/2018 |
| WO | 2018109715 A1 | 6/2018 |
| WO | 2020174051 A1 | 9/2020 |

OTHER PUBLICATIONS

Beauchamp M.S., et al., "Dynamic Electrical Stimulation of Sites in Visual Cortex Produces Form Vision in Sighted and Blind Humans," bioRxiv preprint, Nov. 5, 2018, 24 pages, Retrieved from the Internet: URL: http://dx.doi.org/10.1101/462697.

Donati A.R.C., et al., "Long Term Training with a Brain-Machine Interface Based Gait Protocol Induces Partial Neurological Recovery in Paraplegic Patients," 2016, Scientific Reports 6, Article 30383, 16 pages, Retrieved from the Internet: URL: https://doi.org/10.1038/srep30383.

European Search Report for European Application No. 21168408.9, mailed on Oct. 6, 2021, 4 pages.

Examination Report for German Application No. 1020192014752.6, mailed on Jun. 16, 2020, 8 pages.

Examination Report for German Application No. 102020210676.2, mailed on Apr. 16, 2021, 5 pages.

First Office Action issued Oct. 16, 2019 for German Application No. DE102019202666.4, 16 pages.

Ghai S., et al., "Effect of Rhythmic Auditory Cueing on Parkinsonian Gait: A Systematic Review and Meta-Analysis," Nature Scientific Reports, Jan. 11, 2018, vol. 8, Article 506, DOI:10.1038/s41598-017-16232-5, 19 pages.

Heming E.A., et al., "Designing a Thalamic Somatosensory Neural Prosthesis: Consistency and Persistence of Percepts Evoked by Electrical Stimulation," IEEE Transactions on Neural Systems and Rehabilitation Engineering, IEEE Service Center, New York, US, Oct. 1, 2011, vol. 19 (5), pp. 477-482.

International Search report and Written Opinion in International Application No. PCT/EP2022/059282, mailed on Jul. 11, 2022, 21 pages.

Invitation to Pay Additional Fees and Where Applicable Protest Fee and Partial International Search for PCT/EP2020/055156, mailed on May 29, 2020, 21 pages.

Lee B., et al., "Engineering Artificial Somatosensation Through Cortical Stimulation in Humans," Frontiers in Systems Neuroscience, Jun. 4, 2018, vol. 12, Article 24, 11 pages, www.frontiersin.org.

Roelfsema P.R., et al., "Mind Reading and Writing: The Future of Neurotechnology," Trends in Cognitive Sciences, Elsevier Limited, May 6, 2018, 14 pages, Retrieved from URL: https://doi.org/10.1016/j.tics.2018.04.001.

Rosenthal L., et al., "Sensory Electrical Stimulation Cueing May Reduce Freezing of Gait Episodes in Parkinson's Disease," Hindawi Journal of Healthcare Engineering, 2018, Article ID 4684925, 6 pages.

Swan B.D., et al., "Sensory Percepts Induced by Microwire Array and DBS Microstimulation in Human Sensory Thalamus," Brain Stimulation, Elsevier Incorporated, 2018, vol. 11 (2), pp. 416-422, Retrieved from URL: https://doi.org/10.1016/j.brs.2017.10.017.

Yadav A.P., et al., "A Brain to Spine Interface for Transferring Artificial Sensory Information," 2020, Scientific Reports 10, Article 900, 2020, 15 pages.

European Search Report issued in European Application No. 22151438.3, mailed on Jun. 17, 2022, 4 pages.

* cited by examiner

CLOSED-LOOP AUTOCALIBRATION METHOD FOR A COMPUTER BRAIN INTERFACE DEVICE, COMPUTER PROGRAM AND COMPUTER BRAIN INTERFACE DEVICE

CROSS-REFERENCE TO PRIOR APPLICATIONS

The present application is a continuation-in-part of U.S. patent application Ser. No. 17/224,953, titled ON-LINE AUTOCALIBRATION METHOD FOR A COMPUTER BRAIN INTERFACE DEVICE AND COMPUTER BRAIN INTERFACE DEVICE, filed with the U.S. Patent and Trademark Office on Apr. 7, 2021, and claims priority to European Patent Application No. 22151438.3, filed on Jan. 13, 2022, the entire contents of which are incorporated herein by reference as if fully set forth below in their entirety and for all applicable purposes.

The claims in the instant application are different than those of the parent application and/or other related applications. The Applicant therefore rescinds any disclaimer of claim scope made in the parent application and/or any predecessor application in relation to the instant application. Any such previous disclaimer and the cited references that it was made to avoid, may need to be revisited. Further, any disclaimer made in the instant application should not be read into or against the parent application and/or other related applications.

TECHNICAL FIELD

The present disclosure relates to a closed-loop autocalibration method for a computer brain interface, CBI, device (and other types of neurostimulation equipment) that can be used to adjusts stimulation parameters of the CBI device to ensure—inter alia—robust and consistent information transfer from the CBI device to the brain with high fidelity.

TECHNICAL BACKGROUND

Several promising approaches for implementing a general-purpose CBI are based on implantable neurostimulation systems that typically include one or more neurostimulation electrodes implanted at a desired stimulation site within or close to the nervous system of a person. A neurostimulator (e.g., an implantable pulse generator (IPG)) typically generates neurostimulation signals that are then applied to the neurostimulation electrodes in order to elicit a neural response (e.g., action potentials) in specific parts of the nervous system. For instance, DE 10 2019/202666, US 2020/0269049 and WO 2020/174051 describe such general-purpose CBI devices and systems that use direct neurostimulation of afferent sensory pathways to communicate abstract conceptual information directly to the brain of an individual.

For such CBI devices and systems to work reliably even in normally behaving (e.g. moving) individuals it has to be ensured that a given neurostimulation signal (or sequence of neurostimulation signals) that for instance is associated with a given piece/block of abstract information to be communicated consistently evokes essentially the same neural response in the brain or nervous system of the individual (e.g. a touch sensation in the left hand associated with a movement instruction or balance support cue etc.).

In this context, e.g., due to positional sensitivity a problem occurs, when neurostimulation electrodes that have initially been calibrated to elicit a certain neural response when being provided with a specific neurostimulation signal move relative to the stimulation target (e.g., afferent sensory axons/nerve fibers/neurons terminating in a desired sensory cortex area of the individual). For instance, such a situation may occur when during a movement (e.g., a person changing its body posture from standing to sitting or lying, a person bending over, coughing, etc.) the distance between a spinal cord stimulation electrode and the target nerve fibers in the spinal cord changes. As a result, the same neurostimulation signal that has previously been calibrated for a specific relative orientation and/or distance between electrode and spinal cord nerve fiber will not elicit the same desired neural response. In the prior art this distance is sometimes called dCSF. High bandwidth CBIs typically require complex and fine-tuned neurostimulation signals and thus are affected by such problems more severely than conventional neurostimulation equipment, e.g., for pain treatment etc.

Some aspects of the present disclosure relate to technical improvements/complements to the autocalibration method, device and system disclosed in U.S. patent application Ser. No. 17/224,953.

In addition to the prior art already discussed in for U.S. patent application Ser. No. 17/224,953, U.S. Ser. No. 11,045,129 relates to an implantable device for estimating neural recruitment arising from a stimulus that has a plurality of electrodes. A stimulus source provides stimuli to be delivered from the electrodes to neural tissue. Measurement circuitry obtains a measurement of a neural signal sensed at the electrodes. A control unit is configured to control application of a selected stimulus to neural tissue using the stimulus electrodes and after the selected neural stimulus, apply a probe stimulus having a short pulse width. A remnant neural response evoked by the probe stimulus is measured and the control unit estimates from the remnant neural response a neural recruitment caused by the selected neural stimulus.

Further, U.S. Ser. No. 11,129,991 relates to a system configured to deliver electrical stimulation therapy to a patient, the electrical stimulation therapy comprising a plurality of therapy pulses at a predetermined pulse frequency over a period of time and deliver, over the period of time, a plurality of control pulses interleaved with at least some therapy pulses of the plurality of therapy pulses. The system may also be configured to sense, after one or more control pulses and prior to an immediately subsequent therapy pulse of the plurality of therapy pulses, a respective evoked compound action potential, ECAP, adjust, based on at least one respective ECAP, one or more parameter values that at least partially defines the plurality of therapy pulses, and deliver the electrical stimulation therapy to the patient according to the adjusted one or more parameter values.

U.S. Ser. No. 11,129,987 relates to an Implantable Pulse Generator, IPG, or External Trial Stimulator, ETS, system that is capable of sensing an ECAP, and in conjunction with an external device is capable of adjusting a stimulation program while keeping a location of a Central Point of Stimulation, CPS, constant. Specifically, one or more features of measured ECAP(s) indicative of its shape and size are determined, and compared to thresholds or ranges to modify the electrode configuration of the stimulation program.

Further prior art that forms general technical background of the present disclosure is provided by U.S. Pat. Nos. 9,872,990, 10,926,092, 10,940,316, 10,960,211.

SUMMARY

The methods, devices and systems provided by the prior art have various deficiencies. For instance, they may not allow to perform closed-loop and on-line re-calibration of CBI stimulation parameters or only to a very limited extend. In addition, consistency and long-term stability and/or fidelity of desired artificial sensory perceptions/artificial sensations that are to be elicited in specific sensory cortex areas cannot be ensured with the prior art systems, mainly because in the prior art this technical problem faced by CBI devices does not even arise or does not have the same importance as it has for high bandwidth general purpose CBI applications. In essence, several of the prior art systems discussed above utilize closed-loop methods for detecting neural responses to minimize the occurrence of certain reactions/effects (such as paresthesias, pain etc.). To use an analogy, the prior art systems effectively function similar to audio speakers or headset systems that contain microphones which detect the emitted sound level and will automatically lower the volume if a threshold is reached, thereby protecting the user from unpleasant sensation/high volume sound. By contrast, the stringent fidelity requirements that need to be fulfilled in order to establish a general purpose and high-bandwidth CBI device are of a completely different quality and require a fundamentally different approach.

It is thus a problem underlying the present disclosure to overcome such deficiencies of previous technologies by providing novel closed-loop autocalibration methods for CBI devices and systems.

For instance, while prior art approaches typically involve comparing neural activity recordings (e.g., ECAP recordings) to a "threshold" or a "threshold value" and adjusting stimulation parameters based on determining whether such a threshold is crossed or not, the concept of the existence of a threshold is a simplification that, in some prior art application scenarios may still be sufficient e.g., for suppressing unwanted neural responses, e.g., for pain management or Parkinson Disease management devices.

However, stimulation parameter calibration methods based on this simplification may fail for advanced CBI-paradigms that involve highly consistent high-fidelity stimulation of artificial sensory perceptions as for instance disclosed in US 2020/0269049 and WO 2020/174051. To ensure CBI stimulation fidelity and consistency even in behaving individuals, the inventors of the present disclosure have found that it is instrumental to take into account the fundamental non-linear and dynamic nature of neural excitability when designing stimulation parameter feedback loops.

A key insight of the present disclosure is that already the scientific studies of Hodgkin and Huxley (Nobel prize in physiology 1963) showed that neurons are non-linear dynamical systems, and thus should be treated and interacted with as such, when designing CBI technology and in particular CBI parameter calibration methods and systems. In general, an afferent sensory neuron needs to be described by a set of dynamical variables that describe its state and a dynamical law that describes the evolution of the state variables with time (e.g., a set of coupled differential equations). For example, a proper dynamical description of an afferent sensory neuron may be based on variables describing neuronal dynamics such as a trans-membrane potential, an activation variable of Na+ currents (e.g., ion-channels), an inactivation variable of Na+ currents and activation variable of a fast K+ currents etc. as well as slowly varying adaptation variables, such as an activation of slow voltage- or Ca2+-dependent transmembrane currents. These adaptation variables may change during prolonged neurostimulation and can affect excitability on an intermediate or even on time scales much longer that the duration of a typical action potential and may even change the type of bifurcation behavior and/or phase space topology underlying the excitability of the stimulated afferent sensory neurons used for establishing the CBI channels to the brain.

Embodiments of the present disclosure allow to capture such complex dynamical system behavior of stimulated afferent sensory neurons and to use this information for enhanced closed-loop online calibration of CBI stimulation parameters. For reference, neuronal excitability is extensively reviewed in "*Dynamical Systems in Neuroscience: The Geometry of Excitability and Bursting*"; Eugene M. Izhikevich; The MIT Press, 2007.

Naturally, while discussed in the following with reference to a CBI device, the aspects/embodiments of the present disclosure can also be applied to other types of neurostimulation devices, systems and equipment that might like-wise benefit from the present disclosure, such as DBS devices or spinal cord stimulation devices, etc. that are applied for treating neurological conditions or are used for pain management. Thus, wherever the term "CBI" appears in the following it is to be understood that it also covers such other types of neurostimulation devices, systems and equipment.

For instance, in a first aspect of the present disclosure, a closed-loop calibration method for updating a current set of stimulation parameters of a CBI device is provided that comprises applying, via a neurostimulation interface device operably connected to the CBI device, a burst sequence of stimulation pulses to a plurality of afferent sensory neurons (e.g., of the central nervous system, i.e., of the brain and/or the spinal cord) targeting a sensory cortex area involved with decoding information transmitted by the CBI device, wherein the burst sequence of stimulation pulses is associated with the current set of stimulation parameters and wherein the burst sequence of stimulation pulses is configured to elicit a bioelectric response in the plurality of afferent sensory neurons. The method further comprises recording, via the neurostimulation interface device, the elicited bioelectric response of the stimulated afferent sensory neurons and deriving, based at least in part on the recorded bioelectric response, a neural excitability profile characterizing a non-linear, dynamic excitation behavior of the plurality of afferent sensory neurons corresponding to the applied burst sequence of stimulation pulses and adjusting, based on the derived excitability profile at least one stimulation parameter of the current set of stimulation parameters to obtain an updated set of stimulation parameters.

Importantly, as discussed in more detail below, the derivation of a dynamic excitability profile that is enabled by recording the dynamic bioelectric response associated with a burst sequence of stimulation pulses ensures that non-linear dynamical aspects such as sub-critical bifurcation characteristics, phase space topology as well as time scale separation effects, such as slowly varying (as compared to the action potential dynamics) physiologic adaptations modifying action potential dynamics on medium to long time scales can be appropriately taken into account when adjusting stimulation parameters of the CBI device. In this manner, it can be ensured that the CBI device consistently evokes essentially the same cortical response patterns needed for establishing and maintaining a high CBI channel bandwidth, sensory percept fidelity and information complexity that are all instrumental for general purpose CBI performance.

For instance, the burst sequence of stimulation pulses may be part of a neurostimulation signal or a signal sequence, applied by the CBI device to elicit an artificial sensory perception in a sensory cortex area receiving input signals from a subset of the plurality of afferent sensory neurons (e.g., for communicating abstract semantic information or for high fidelity sensory substitution or enhancement). In this manner, for example, no dedicated calibration signals are required, and the excitability profile directly corresponds to the actual operation conditions/parameters of the CBI device.

Further, the burst sequence of stimulation pulses may comprise a burst sequence of essentially identical and/or phasic stimulation pulses. Further, the intra-burst pulse frequency may be at least 50 Hz, preferably at least 100 Hz, more preferably at least 200 Hz and even more preferably at least 250 Hz. For instance, using such pulse parameters allows to characterize the dynamic excitation behavior and certain phase-space properties such as a bifurcation type, phase-space topology, limit-cycle behavior etc. that otherwise could not be taken into account when adjusting stimulation parameters.

Further, a typical value for a burst repetition rate may be 1 to 10 Hz and for a pulse count within a burst sequence may be in the range of 3 to 50, preferably in the range of 5 to 25. For instance, to improve characterization of the non-linear excitability behavior of the stimulated neurons, intra-burst frequency should correspond to the refractory period of the neurons and/or burst repetition rate should allow to capture the slow dynamics of physiologic adaptation processes.

Further, recording the elicited dynamic bioelectric response may comprises recording the bioelectric response while the sequence of stimulation pulses is being applied, preferably after each stimulation pulse or continuously during the sequence and wherein deriving the excitability profile is based at least in part on intra-burst variations of the recorded bioelectric response. Further, a sampling rate of the recording may be larger or equal to the inverse of the time duration between two stimulation pulses of the sequence of stimulation pulses, preferably at least twice as large, more preferably at least 10 times as large and even more preferably at least 100 times as large. For example, preferably, the recording sampling rate may be at least 30 kHz or at least 100 kHz.

Using such recoding techniques and recoding parameters further enhances how the dynamic excitation behavior of the stimulated plurality of afferent sensory neurons can be characterized.

Further, in particular for being more sensitive to slow physiologic adaptation effects and/or for deriving non-trivial properties of the phase space of the non-linear excitation dynamics, in some embodiments, at least two consecutive burst sequences may be applied, and deriving the excitability profile may be based at least in part on analyzing inter-burst variations of the recorded bioelectric response(s). Optionally, stimulation parameters such as intra-burst pulse frequency, amplitude, polarity, etc. may be varied among the at least two consecutive burst sequences.

For instance, varying the pulse frequency (e.g., of a sequence of individually sub-critical pulses) among consecutive burst sequences may allow to characterize non-linear dynamic phenomena such as non-linear resonances, phase-locking, synchronization, Arnold tongues, bifurcation types, etc.

For example, in some embodiments, deriving the dynamic excitability profile may be based at least in part of correlating the recorded bioelectric response with predictions of a non-linear mathematical model of neuronal excitability, comprising model parameters that vary slowly in time to capture physiologic adaptation mechanisms of the stimulated afferent sensory neurons.

For similar reasons as above, in some embodiments, at least two burst sequences may be applied and deriving the dynamic excitability profile may comprises analyzing the bioelectric response(s) corresponding to each stimulation pulse within a burst sequence as well as the joint or total bioelectric response corresponding to each burst sequence. Additionally of alternatively deriving the excitability profile may comprises analyzing variations among the recorded bioelectric responses within one burst sequence and/or among consecutive burst sequences.

To further improve, at least in some embodiments, the characterization of the non-linear excitability properties of the stimulated neurons, deriving the excitation profile may also comprise extracting temporal variations or dynamics of recording signal parameters or derived metrics from a plurality of subsequent recordings of the elicited bioelectric response and/or continuous recordings and/or classifying the excitation behavior of a subset of the stimulated afferent sensory neurons may use a closed set of discrete categories and based at least in part on the derived excitability profile.

For instance, such classification into excitability categories may be based on a metric (such as an absolute value or levels) for one or more signal parameters extracted from the recorded bioelectric responses. In addition, such classification may also be based on dynamical properties such as the type of bifurcation behavior (e.g., sub-critical Poincaré-Andronov-Hopf bifurcation, saddle-node bifurcation etc.) underlying the non-linear behavior of the stimulated afferent sensory neurons. In other examples, such classification may also quantify in a discrete manner the distance (e.g., in phase space) from generating an action potential. Optionally, classification may also be based at least in part on analyzing a temporal variation or dynamic of the excitability profile within one burst sequence of stimulation pulses and/or among consecutive burst sequences of stimulation pulses.

In some aspects, the elicited bioelectric response(s) may comprise one or more compound action potentials, CAPs, and deriving the excitability profile may comprise determining one or more of: an N1/P2 amplitude; a number of detectable peaks or minima, a measure of synchrony (in time) among the CAP responses within the sequence or among subsequent sequences of stimulation pulses and/or a delay between a stimulation pulse and the corresponding CAP response.

Further, adjusting the at least one stimulation parameter may comprise, at least in some embodiments, comparing the derived excitability profile with a reference excitability profile.

For example, the reference excitability profile may include one or more of the following information: an amplitude of a reference bioelectric response, intra-burst variations among bioelectric responses corresponding to single stimulation pulses within a burst sequence, intra-burst variations of the bioelectric response corresponding to the first and the last stimulation pulse within a burst stimulation sequence and inter-burst variations of the bioelectric response.

As discussed in detail in application Ser. No. 17/224,953 such a reference bioelectric response may be stored in a non-transitory memory medium of the CBI device or obtained via a communication interface of the CBI device. Accordingly, in some embodiments, the reference excitability profile may correspond to a specific artificial sensory perception corresponding to a set of reference stimulation parameters associated with the reference excitability profile.

Further, a neurostimulation signal or signal sequence may be applied to a subset of the afferent sensory neurons using the updated stimulation parameters wherein the neurostimulation signal may be configured to elicit an artificial sensory perception/percept in a sensory cortex area receiving afferent sensory input from the stimulated subset of afferent sensory neurons.

Further, in some embodiments, the calibration method discussed above may incorporate other types physiological signals such as myogenic potentials or recordings from cortical areas as feedback information.

In a further aspect, the present disclosure also provides a computer program (e.g., stored on a memory device or memory medium) comprising instructions for carrying out a method according to any of the embodiments discussed above, when these instructions are executed by data and signal processing circuitry of a computer brain interface device, e.g., operably connected to an IPG via a wireless communication interface, such as Bluetooth.

Further a computer brain interface, CBI, device is provided that comprises data and signal processing circuitry for carrying out a method according to any of the embodiments discussed above, e.g., when carrying out the instructions of a computer program as discussed above.

In some aspects, such a CBI device may comprise one or more stimulation and sensing channels adapted to elicit and sense a bioelectric response of one or more afferent sensory neurons terminating (e.g. mono- or multi-synaptically) in a sensory cortex area. Such a CBI device may further comprise a non-transitory memory medium operably connected to the data and signal processing circuitry storing a first mapping between one or more artificial sensations that can be elicited by the CBI device in one or more sensory cortex areas of the individual and one or more bioelectric responses and/or storing a second mapping between a plurality of sets of neurostimulation signal parameters and a plurality of bioelectric responses of the one or more afferent sensory neurons (e.g. recorded upon initial calibration and/or during on-line recalibration as outline above).

SHORT DESCRIPTION OF THE FIGURES

Figure 2:
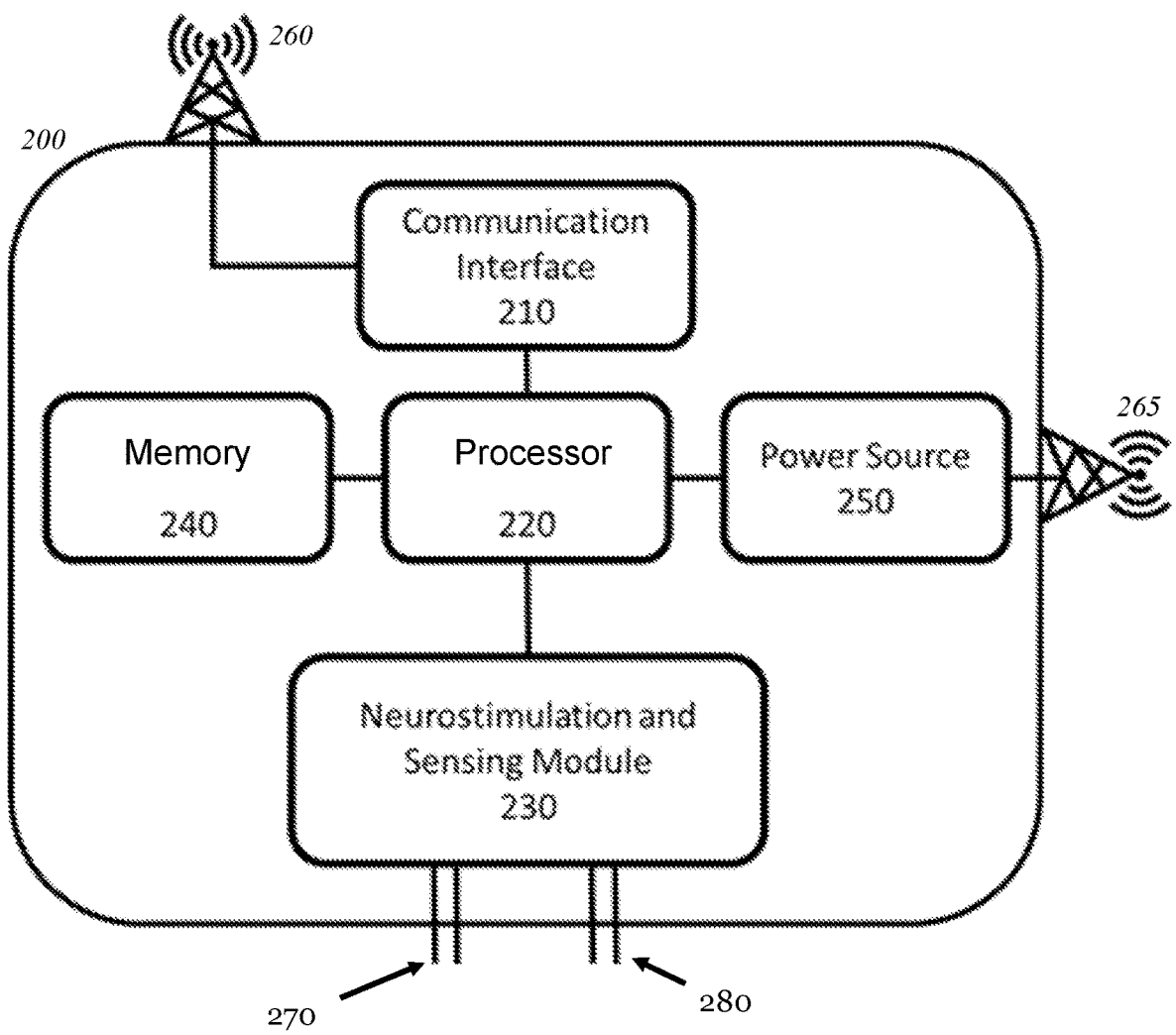
Figure 3:
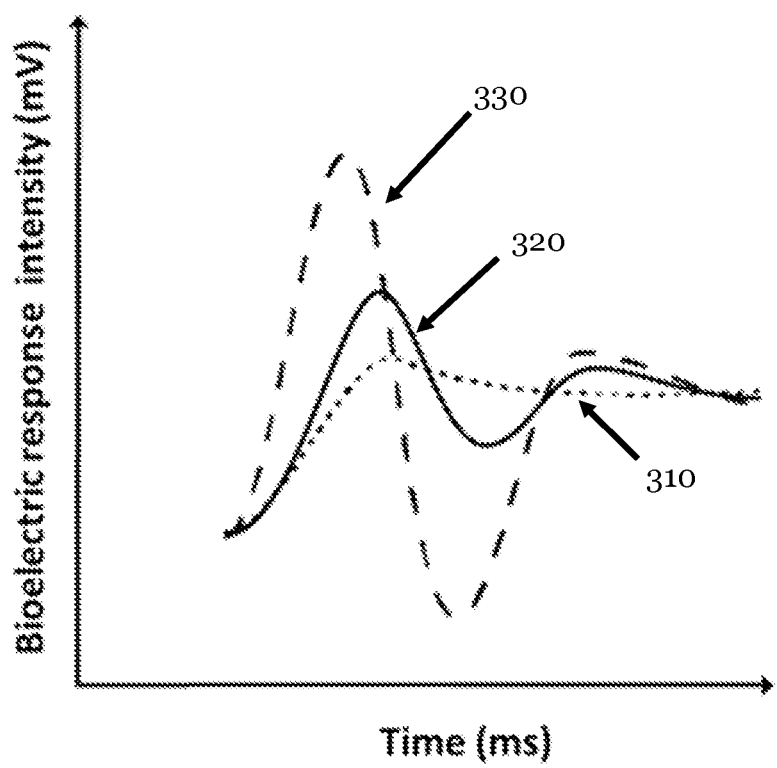

Various aspects of the present disclosure are described in more detail in the following by reference to the accompanying figures. These figures show:

FIG. 1 a diagram illustrating an individual being equipped with a CBI device, according to some embodiments;

FIG. 2 a functional block circuit diagram illustrating a CBI device, according to some embodiments FIG. 3 a diagram illustrating a set of dynamic bioelectric responses recorded from afferent sensory neurons, according to some embodiments.

Figure 4:
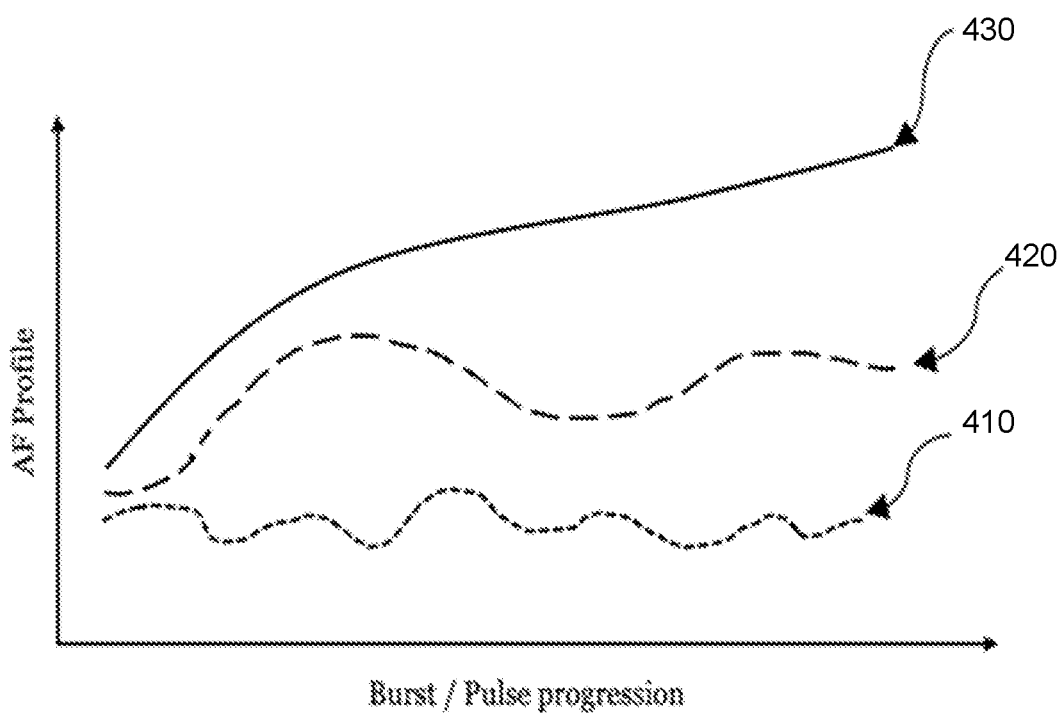
Figure 5:
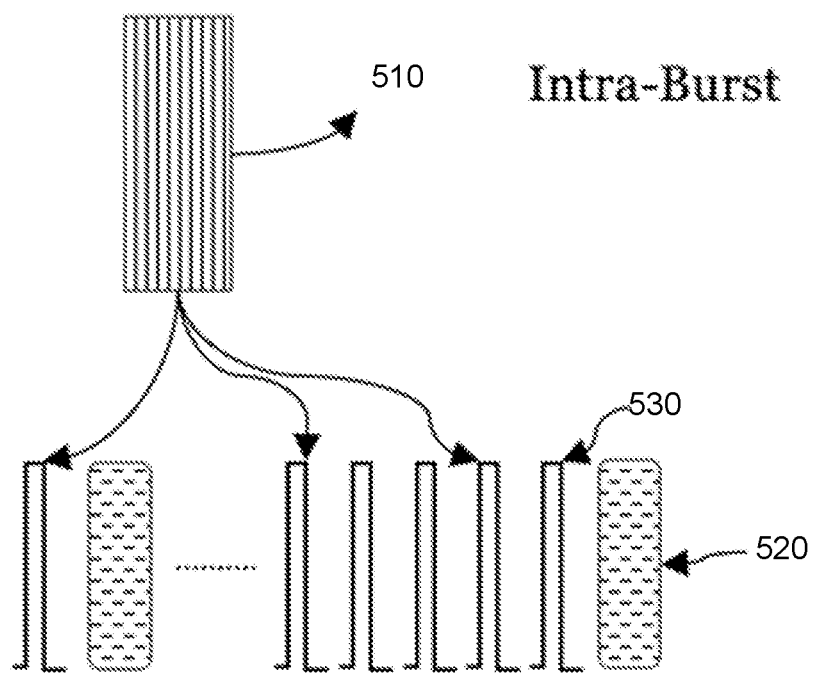
Figure 6:
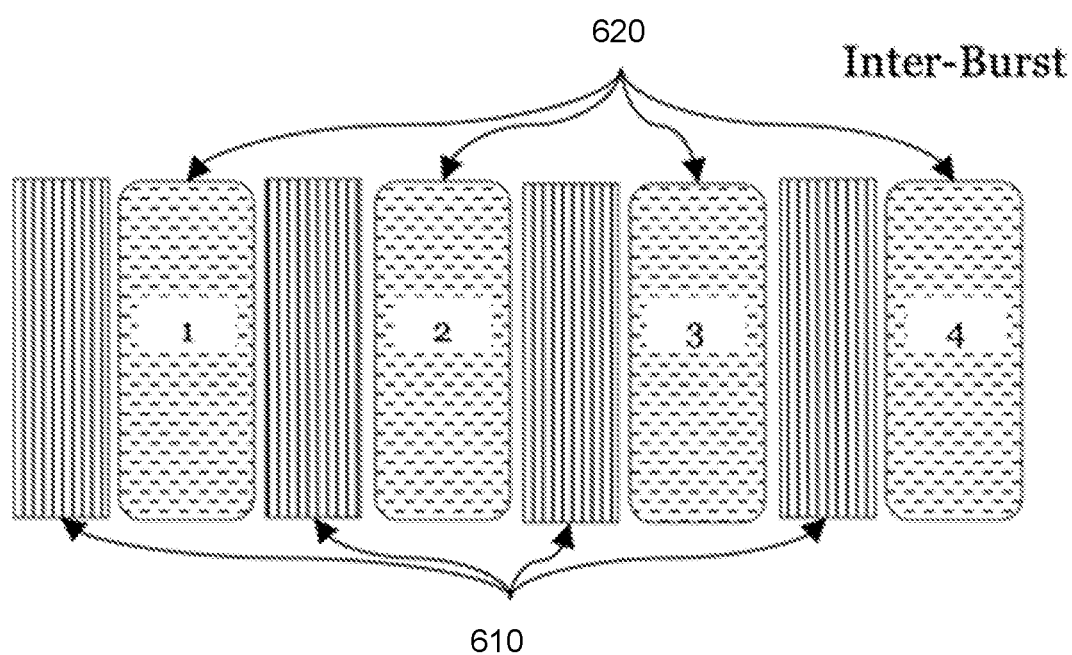
Figure 7:
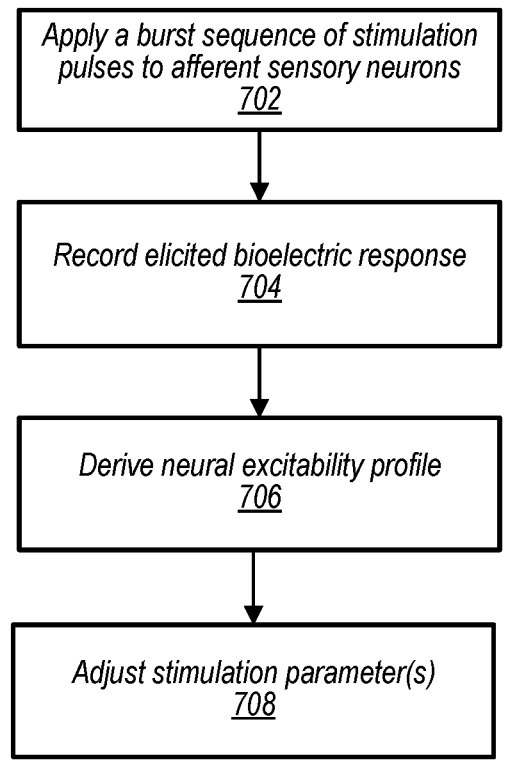

FIG. 4 a diagram illustrating examples of temporally varying excitability profiles, according to some embodiments;

FIG. 5 a diagram illustrating a basic example of intra-burst recording, according to some embodiments;

FIG. 6 a diagram illustrating a basic example of inter-burst recording, according to some embodiments FIG. 7 a flowchart diagram illustrating a method for adjusting a stimulation parameter, according to some embodiments.

DETAILED DESCRIPTION OF SOME EXEMPLARY EMBODIMENTS

In the following, some exemplary embodiments of the present disclosure are described in more detail, with reference to a CBI device that can be interfaced with neurostimulation electrodes such as spinal cord stimulation electrodes and/or DBS electrodes, e.g., via an intermediate neurostimulation device. However, the present disclosure can also be used with any other neurostimulation interface that is capable of stimulating afferent sensory neurons (e.g., axons, nerve fibers, etc.) of the central or peripheral nervous system targeting directly or indirectly a sensory cortex area of an individual.

While specific feature combinations are described in the following paragraphs with respect to the exemplary embodiments of the present disclosure, it is to be understood that not all features of the discussed embodiments have to be present for realizing the disclosure, which is defined by the subject matter of the claims. The disclosed embodiments may be modified by combining certain features of one embodiment with one or more technically and functionally compatible features of other embodiments. Specifically, the skilled person will understand that features, components and/or functional elements of one embodiment can be combined with technically compatible features, components and/or functional elements of any other embodiment of the present disclosure as long as covered by the invention specified by the appended claims.

Moreover, the various modules of the devices and systems disclosed herein can for instance be implemented in hardware, software or a combination thereof. For instance, the various modules of the devices and systems disclosed herein may be implemented via application specific hardware components such as application specific integrated circuits, ASICs, and/or field programmable gate arrays, FPGAs, and/or similar components and/or application specific software modules being executed on multi-purpose data and signal processing equipment such as CPUs, DSPs and/or systems on a chip, SOCs, or similar components or any combination thereof.

For instance, the various modules of the CBI devices discussed herein above may be implemented on a multi-purpose data and signal processing device (e.g., a smart phone) configured for executing application specific software modules and for communicating with various sensor devices and/or neurostimulation devices or systems via conventional wireless communication interfaces such as a NFC, a WIFI and/or a Bluetooth interface.

Alternatively, the various modules of the CBI devices discussed in the present application may also be part of an integrated neurostimulation apparatus, further comprising specialized electronic circuitry (e.g. neurostimulation signal generators, amplifiers etc.) for generating and applying the determined neurostimulation signals to a neurostimulation interface of the individual (e.g. a multi-contact electrode, a spinal cord stimulation electrode, peripheral sensory nerve stimulation electrode etc.) and for recoding the bioelectric responses as disclosed herein.

As discussed above the present disclosure may be realized in situations where the perceptual channels of a general-purpose CBI are not calibrated via subject-experimenter interactions. Instead, the CBI stimulation parameters can be self-calibrated by tapping into the neural activity of the tissue in vicinity of the stimulation interface. For instance, the level of induced bioelectric activation can be measured by interleaving recording bioelectric responses elicited by burst sequences of stimulation pulses.

In some examples, also described in application Ser. No. 17/224,953 special test waveforms may be defined by modulating various aspect of the waveform in bursting mode. The modulated parameters of the waveform may include but are not limited to: a spatial activation pattern of the electrode contacts, an amplitude, an inter-pulse frequency, an inter-burst frequency, a pulse width, a wave-form shape (e.g. mono-phasic, biphasic with symmetric or with long active discharge period, multiphasic, etc.), a density of pulses within a burst or a burst duration. In an exemplary stimulation paradigm, a few symmetric pulses (e.g., in a range of 4-9 pulses) are delivered within short bursts (e.g., lasting 40 ms-60 ms) to convey information related to intensity of sensation. The intensity can then be varied at a second measurement of loci point in time by changing density of pulses per burst while keeping pulse numbers constant i.e. shortening duration but increase intra-burst frequency and vice-versa.

For instance, neural recordings/sensing of bioelectric responses may take place by ramping stimulation signal bursts in repetition, aggregate frequency power pre- and post-pulse for each step of the ramp across repeated bursts then create differential response profile to pulses with varied intensity for the same purpose, so that the CBI device can estimate the neural excitation behavior of the stimulated afferent sensory nerve fibers by fitting a response function to the amplitude of the ECAP or theta frequency band of the ECAPs taking into account the response at every intensity increment. As stated above the excitation behavior can also be estimated not only by varying the amplitude of the burst in a ramp by also by changing other parameters of the stimulation such as frequency, pulse width, as well as the inter burst intervals, for example.

The estimated dynamic excitability profile then allows to determine improved stimulation parameters which are adequate to generate a desired level of activity in the target tissue thereby stabilizing the intensity, locus and/or quality of artificial sensory perceptions in the targeted sensory cortex area. This may be achieved, for example, by determining the highest value parameter coefficients which crucially contribute to determination of sensation intensity.

FIG. 1 illustrates a person/individual 100 that is equipped with a CBI device as described in section 3 "Summary" above. In the illustrated embodiment, the CBI is implemented via direct neurostimulation of afferent sensory nerve fibers/neurons in the spinal cord 106 via one or more multi-contact electrodes 104 driven by an IPG 102 that may be operatively connected to or integrated with a CBI device as disclosed herein.

For establishing a perceptual communication channel to the brain of the individual 100 the CBI device typically is calibrated such that neurostimulation signals generated by the CBI device and applied via the IGP 102 and the multi-contact electrode 104 elicit one or more action potentials 108 in one or more afferent sensory nerve fibers of the spinal cord 106 targeting (e.g. via multi-synaptic afferent sensory pathways) one or more sensory cortex areas 110 of the individual where the one or more action potentials 108 generate artificial sensory perceptions that can be used to communicate with the individual 100. As discussed in detail in US 2020/0269049, fully incorporated herein by reference, artificial sensory perceptions that are elicited in a sensory cortex area (e.g., a sensory cortex area processing touch sensation on the left or right hand) can be associated with any kind of abstract information that is intelligible (i.e., consciously or subconsciously) by the individual.

While FIG. 1 shows orthodromically recoding, bioelectric responses may also be recorded differently, such as antiorthodromically.

FIG. 2 shows an exemplary CBI device according to an embodiment of the present invention. In this embodiment, the CBI device comprises an integrated neurostimulation and sensing module 230 (e.g. comprising a neuronal signal generator and an output amplifier as well as a sensing amplifier and an analog to digital converted) that is connected to a plurality of output signal leads 270 and a plurality of separate or identical sensing signal leads 280 that may be interfaced with a neurostimulation interface of the individual (e.g. a multi-contact spinal cord stimulation electrode such as the electrode 104 shown in FIG. 1). The CBI device may further comprise a communication antenna 260 operably connected to a communication interface module 210, configured for wireless communication (e.g., via NFC, Bluetooth, or a similar wireless communication technology).

The communication interface module 210 may be configured, for example, to receive one or more sensor signals from one or more sensors (not shown; e.g., acceleration signals obtained form an accelerometer etc.) and/or control information from a control device such as a remote control or a smart phone. The communication interface module 210 is operably connected to a data/signal processor 220 configured to generate one or more neurostimulation signals and/or signal parameters (e.g., waveform, pulse shape, amplitude, frequency, burst count, burst duration etc.) for generating the one or more neurostimulation signals. For instance, the processor 220 may access a data storage memory medium 240 configured to store a plurality of relations, specific for the individual, associating a plurality of neurostimulation signals (or parameters used for generating a plurality of neurostimulation signals) with a plurality of corresponding pieces of information to be communicated to the individual.

The generated neurostimulation signals and/or the signal parameters are input into the integrated neurostimulation and sensing module 230 that may be configured to process (e.g., modulate, switch, amplify, covert, rectify, multiplex, phase shift, etc.) the one or more neurostimulation signals generated by the processor 220 or to generate the one or more neurostimulation signals (e.g., burst sequences of stimulation pulses as discussed in the present disclosure) based on the signal parameters provided by the processor 220.

The generated and processed neurostimulation signals are then output by the neurostimulation and sensing module 230 and can be applied to one or more electric contacts of a neurostimulation electrode (e.g., a DBS electrode or spinal cord stimulation electrode as shown in FIG. 1) via output leads 270. The CBI device of FIG. 2 may also comprise a rechargeable power source 250 that, for instance may be wirelessly charged via a wireless charging interface 265.

As discussed above, the data/signal processor 220 may be further configured to, e.g., in conjunction with the data storage memory medium 240 and the neurostimulation and sensing module 230, to execute a closed-loop, on-line auto-calibration method as discussed and detail above and below. For example, it may generate one or more burst sequences of stimulation pulses (for examples see FIG. 5 and FIG. 6 below) configured to elicit a bioelectric response in one or more afferent sensory nerve fibers/neurons such as an evoked (compound) action potential in one or more afferent sensory nerve fibers/neurons of the spinal cord 106 as shown in FIG. 1.

The burst sequences of stimulation pulses may then be applied via output stimulation leads 270 to a neurostimulation interface such as the most caudal contact 112 of the multi-contact electrode 104 shown in FIG. 1. The neurostimulation and sensing module 230 may then sense, via the neurostimulation interface (e.g., via the most rostral contact 114), a bioelectric response 108 of the stimulated afferent sensory nerve fiber of the spinal cord 106.

Based on the sensed bioelectric response(s), the excitation behavior of the stimulated afferent sensory nerve fibers/neurons with respect to the neurostimulation interface can then be estimated by the neurostimulation and sensing module 230 and/or the processor 220. As discussed above (e.g., see section 3 "summary"), based on the sensed bioelectric responses, a dynamic excitability profile can be derived and used for closed-loop stimulation parameter adaptation and/or stored in data storage memory medium 240 for later use, e.g., for determining slowly varying physiologic adaptation processes as discussed above.

FIG. 3 illustrates exemplary bioelectric responses 310, 320, 330 (e.g., extracellularly sensed (E)CAPs) of a subpopulation of afferent sensory nerve fibers/neurons (e.g., of the spinal cord 106; see FIG. 1) sensed and recorded during application of a burst sequence of stimulation pulses according to aspects of the present disclosure (e.g., applied via the multi-contact spinal cord stimulation electrode 104 shown in FIG. 1) driven by a CBI device (see FIG. 2) according to an embodiment of the present disclosure. The illustrated bioelectric responses are sensed/recorded while several (e.g., consecutive) pulses within a burst sequence (see for example FIG. 5 below) are applied. Although the stimulation parameters for each pulse are kept constant, the bioelectric response changes substantially due to the non-linear nature of neuronal excitability as discussed above.

Based on such recordings of bioelectric responses the temporal dynamics of neuronal excitability can be derived and used for deriving the excitability profiles discussed in detail above.

FIG. 4 illustrates three examples of such excitability profiles. On the x-axis pulse progression within a burst or several subsequent bursts is indicated. On the y-axis an excitation profile parameter such as the amplitude of the first peak or the difference of the second peak and the first valley or the delay between pulse and first peak or any other suitable recording signal parameter or metric as discussed above is plotted as a function of burst progression.

The three exemplary traces 410, 420 and 430 may correspond to three different burst sequences each using different stimulation parameters. For instance, trace 410 may correspond to a set of parameters that do not result in (compound) action potential generation, trace 420 may correspond to a set of parameters that may result in inconsistent excitation behavior and trace 430 may correspond to a set of parameters that consistently evoke (compound) action potentials in a subset of the stimulated plurality of afferent sensory nerve fibers/neurons. In other situations, the three traces may also be recorded in subsequent stimulation trials with essentially identical pulse parameters, e.g., in situation where slow physiologic changes fundamentally shift the dynamic excitation behavior of the stimulated neurons.

As can be seen from FIG. 4, deriving a whole excitability profile may be desirable to determine with high probability which set of stimulation parameters actually results in consistent action potential generation and thus should be used for operating the CBI device to transmit information to the brain. For instance, just comparing the initial part of the three traces may not result in an accurate characterization of the excitation behavior and could thus result in undesirably adjusted stimulation parameters.

Auto-calibration of the perceptual channels of the CBI device may then be achieved by using a neural interface device capable of stimulation and recording from the neural tissue. The derived excitability profiles and their dynamics may be compared after each individual stimulation pulse within a burst and/or between bursts in a trial to automatically determine the effectiveness of stimulation settings and establish various sensation levels within perceptual channels. Given similar stimulation parameters in each burst, the inter-burst dynamics of the excitability profile 430 exhibit a distinct shape compared to an undesired excitability profile as a function of burst progression. It should be noted that although profile 420 may (locally) exhibit a higher intensity response, the stimulation does not maintain an increasing profile evolution.

FIG. 5 illustrates an intra-burst sequence recording configuration where the CBI device delivers (e.g., via a neurostimulation module; see FIG. 2) or commands an implanted stimulator to deliver a burst 510 of essentially identical stimulation pulses and records the induced bioelectric responses (e.g., action potentials, ECAPs, etc.) while the burst is applied. For instance, the induced bioelectric responses may be recorded 520 after the first and after the last stimulation pulse 530. In other embodiments, recordings may take place after each stimulation pulse within the burst or throughout in an essentially continuous manner (e.g., with a sampling rate of 100 kHz) as discussed above.

FIG. 6 illustrates an inter-burst sequence recording configuration where the CBI device delivers (e.g., via a neurostimulation module; see FIG. 2) or commands an implanted stimulator to deliver a sequence of bursts 610 of essentially identical stimulation pulses and records 620 the induced bioelectric responses (e.g., action potentials, ECAPs, resting potential, depolarization, etc.) after each burst sequence and optionally, also while each burst sequence is applied as illustrated in FIG. 5 and discussed above. Such a stimulation and recording sequence may enable the CBI to detect slowly varying variables that might affect neuronal excitability on medium to long time scales as also discussed above.

FIG. 7 is a flow chart diagram illustrating a method for a device such as a neurostimulation (NS) or computer brain interface (CBI) device and/or a system to adjust one or more stimulation parameters of stimulation pulses to be provided to an individual, according to various embodiments. Aspects of the method of FIG. 7 may be implemented by a wireless device, such as the CBI device 200, in communication with one or more implanted neurostimulation devices, as illustrated in and described with respect to the Figures, or more generally in conjunction with any of the computer systems or devices shown in the Figures, among other circuitry, systems, devices, elements, or components shown in the Figures, among other devices, as desired. For example, one or more processors (or processing elements) of the device (e.g., processor(s) 220, baseband processor(s), processor(s) associated with communication circuitry, etc., among various possibilities) may cause the device to perform some or all of the illustrated method elements. The device may be configured with a non-transitory computer-readable memory medium, such has memory 240, which stores program instructions which are executable by the processor to perform the described method steps. In various embodiments, some of the elements of the methods shown may be performed concurrently, in a different order than shown, may be substituted for by other method elements, or may be omitted. Additional method elements may also be performed as desired. As shown, the method may operate as follows.

At 702, a burst sequence of stimulation pulses is applied, via a neurostimulation interface device operably connected to the device, to a plurality of afferent sensory neurons of an individual targeting a sensory cortex area involved with decoding information transmitted by the device. The sequence of stimulation pulses may be associated with the current set of stimulation parameters. The sequence of stimulation pulses may be configured to elicit a bioelectric response in the plurality of afferent sensory neurons. Subsequent stimulation pulses of the burst sequence may modify one or more parameters such as the waveform, pulse shape, amplitude, frequency, burst count, and/or burst duration, etc., to probe the non-linear dynamic excitation behavior of the afferent sensory neurons.

The burst sequence of stimulation pulses may be part of a neurostimulation signal or signal sequence applied by the device to elicit an artificial sensory perception in a sensory cortex area receiving input signals from at least a subset of the plurality of afferent sensory neurons. The burst sequence of stimulation pulses may be a burst sequence of essentially identical pulses and/or phasic stimulation pulses, and an intra-burst pulse frequency may be at least 50 Hz, in some embodiments.

At 704, the elicited bioelectric response of the stimulated afferent sensory neurons is recorded via the neurostimulation interface device. The bioelectric response is elicited by the burst sequence of stimulation pulses. In various embodiments, the elicited bioelectric response may be recorded in either an intra-burst manner as shown in FIG. 5, where the response is recorded subsequent to applying the burst sequence of stimulation pulses, or in an inter-burst manner as shown in FIG. 6, where bioelectric responses are recorded in between stimulation pulses of the burst sequence. For example, recording the elicited bioelectric response may involve recording the bioelectric response while the burst sequence of stimulation pulses is being applied. In these embodiments, deriving the neural excitability profile at step 706 may be based at least in part on analyzing intra-burst variations of the recorded bioelectric response. In some embodiments, a sampling rate of the recording is equal or larger than an inverse of a time duration between two stimulation pulses of the burst sequence of stimulation pulses.

At 706, a neural excitability profile is derived based at least in part on the recorded bioelectric response. The neural excitability profile characterizes a non-linear, dynamic excitation behavior of the plurality of afferent sensory neurons corresponding to the applied sequence of stimulation pulses. In general, afferent sensory neurons exhibit complex, non-linear and dynamic excitation behavior in response to stimulation pulses. The applied sequence of stimulation pulses may be used to probe this complex excitation behavior, by applying a burst sequence of stimulation pulses with modified parameters, as described above. The processor may derive the neural excitability profile by determining how the excitation behavior changes with various modifications to the stimulation pulses.

In some embodiments, two or more consecutive burst sequences may be applied, and deriving the excitability profile may be performed based at least in part on analyzing inter-burst variations of the recorded bioelectric response. Stimulation parameters of the consecutive burst sequences may be modified. For example, the pulse frequency may be varied between different consecutive burst sequences, among other possibilities. In some embodiments, deriving the excitability profile includes analyzing the bioelectric response corresponding to each stimulation pulse within each burst sequence, and analyzing variations among the recorded bioelectric responses within one burst sequence or among consecutive burst sequences.

In some embodiments, deriving the excitation profile involves extracting temporal variations or dynamics of recording signal parameters or derived metrics from a plurality of subsequent recordings of the elicited bioelectric response. The excitation behavior of a subset of the stimulated afferent sensory neurons may be classified using a closed set of discrete categories. Classification may be based at least in part on analyzing a temporal variation or dynamic of the excitability profile within one burst sequence of stimulation pulses or among consecutive burst sequences of stimulation pulses. Deriving the excitability profile may be based at least in part on correlating the recorded bioelectric response with predictions of a non-linear mathematical model of neuronal excitability. The non-linear mathematical model may include model parameters that vary slowly in time to capture physiologic adaptation mechanisms of the stimulated afferent sensory neurons.

In some embodiments, the elicited bioelectric response includes one or more compound action potentials (CAPs), and deriving the excitability profile includes determining one or more of an N1/P2 amplitude, a number of detectable peaks or troughs, a measure of synchrony among the bioelectric responses recorded for the burst sequence or among subsequent burst sequences of stimulation pulses, and a delay between a stimulation pulse and the corresponding CAP.

At 708, at least one stimulation parameter of the current set of stimulation parameters is adjusted to obtain an updated set of stimulation parameters. The stimulation parameter(s) may be adjusted based on the derived neural excitability profile. The stimulation parameter(s) may be adjusted to improve the provision of information to the individual through the stimulation pulses. For example, the neural excitability profile may be analyzed to determine that a stimulation parameter is miscalibrated, such that a stimulation pulse intended to elicit a particular artificial sensory perception elicits an actual artificial sensory perception that is different than what is intended. In this example, a stimulation parameter used to generate the stimulation pulse may be modified to remove or reduce the discrepancy between the desired artificial sensory perception and the actual artificial sensory perception.

Said another way, in some embodiments, adjusting the at least one stimulation parameter is performed by comparing the derived excitability profile with a reference excitability profile. The reference excitability profile may include an amplitude of a reference bioelectric response, intra-burst variations among bioelectric responses corresponding to single stimulation pulses within a burst sequence, and/or intra-burst variations of the bioelectric response corresponding to the first and the last stimulation pulse within a burst stimulation sequence. In some embodiments, the reference excitability profile corresponds to a specific artificial sensory perception corresponding to a set of reference stimulation parameters associated with the reference excitability profile.

In some embodiments, subsequent to updating the stimulation parameters, a neurostimulation signal or signal sequence may be applied to at least a subset of the afferent sensory neurons using the updated stimulation parameters. The neurostimulation signal or signal sequence may be configured to elicit an artificial sensory perception in a sensory cortex area receiving afferent sensory input from the stimulated subset of afferent sensory neurons.

What is claimed is:

1. A closed-loop calibration method for updating a current set of stimulation parameters of a device, the method comprising, by a processor:

applying, via a neurostimulation interface device operably connected to the device, a burst sequence of stimulation pulses to a plurality of afferent sensory neurons targeting a sensory cortex area involved with decoding information transmitted by the device, wherein the sequence of stimulation pulses is associated with the current set of stimulation parameters, and wherein the sequence of stimulation pulses is configured to elicit a bioelectric response in the plurality of afferent sensory neurons;

recording, via the neurostimulation interface device, the elicited bioelectric response of the stimulated afferent sensory neurons;

deriving, based at least in part on the recorded bioelectric response, a neural excitability profile characterizing a non-linear, dynamic excitation behavior of the plurality of afferent sensory neurons corresponding to the applied sequence of stimulation pulses; and adjusting, based on the derived excitability profile, at least one stimulation parameter of the current set of stimulation parameters to obtain an updated set of stimulation parameters.

2. The method of claim 1,
wherein the burst sequence of stimulation pulses is part of a neurostimulation signal or signal sequence applied by the device to elicit an artificial sensory perception in a sensory cortex area receiving input signals from at least a subset of the plurality of afferent sensory neurons,
wherein the burst sequence of stimulation pulses comprises a burst sequence of essentially identical pulses and/or phasic stimulation pulses; and
wherein an intra-burst pulse frequency is at least 50 Hz.

3. The method of claim 1,
wherein recording the elicited bioelectric response comprises recording the bioelectric response while the burst sequence of stimulation pulses is being applied, and
wherein deriving the excitability profile is based at least in part on analyzing intra-burst variations of the recorded bioelectric response.

4. The method of claim 3,
wherein bioelectric response is recorded after each stimulation pulse or continuously during the sequence.

5. The method of claim 1, wherein a sampling rate of the recording is equal or larger than an inverse of a time duration between two stimulation pulses of the burst sequence of stimulation pulses.

6. The method of claim 1,
wherein at least two consecutive burst sequences are applied, and
wherein deriving the excitability profile is based at least in part on analyzing inter-burst variations of the recorded bioelectric response.

7. The method of claim 6,
wherein one or more stimulation parameters including a pulse frequency are varied among the at least two consecutive burst sequences.

8. The method of claim 1,
wherein at least two burst sequences are applied,
wherein deriving the excitability profile comprises analyzing the bioelectric response corresponding to each stimulation pulse within each burst sequence, and
wherein deriving the excitability profile comprises analyzing variations among the recorded bioelectric responses within one burst sequence or among consecutive burst sequences.

9. The method of claim 1,
wherein deriving the excitation profile comprises extracting temporal variations or dynamics of recording signal parameters or derived metrics from a plurality of subsequent recordings of the elicited bioelectric response, and
wherein the method further comprises, by the processor:
classifying the excitation behavior of a subset of the stimulated afferent sensory neurons using a closed set of discrete categories and based at least in part on the derived excitability profile.

10. The method of claim 9,
wherein classification is based at least in part on analyzing a temporal variation or dynamic of the excitability profile within one burst sequence of stimulation pulses or among consecutive burst sequences of stimulation pulses.

11. The method of claim 1,
wherein deriving the excitability profile is based at least in part on correlating the recorded bioelectric response with predictions of a non-linear mathematical model of neuronal excitability,
wherein the non-linear mathematical model comprises model parameters that vary slowly in time to capture physiologic adaptation mechanisms of the stimulated afferent sensory neurons.

12. The method of claim 1,
wherein the elicited bioelectric response comprises one or more compound action potentials (CAPs), and
wherein deriving the excitability profile comprises determining one or more of:
a difference of a second peak and a first valley within the elicited bioelectric response,
a number of detectable peaks or troughs,
a measure of synchrony among the bioelectric responses recorded for the burst sequence or among subsequent burst sequences of stimulation pulses, and
a delay between a stimulation pulse and the corresponding CAP.

13. The method of claim 1,
wherein adjusting the at least one stimulation parameter comprises comparing the derived excitability profile with a reference excitability profile,
wherein the reference excitability profile includes one or more of the following:
an amplitude of a reference bioelectric response,
intra-burst variations among bioelectric responses corresponding to single stimulation pulses within a burst sequence, and
intra-burst variations of the bioelectric response corresponding to the first and the last stimulation pulse within a burst stimulation sequence.

14. The method of claim 13,
wherein the reference excitability profile corresponds to a specific artificial sensory perception corresponding to a set of reference stimulation parameters associated with the reference excitability profile.

15. The method of claim 1, the method further comprising, by the processor:
applying, via the neurostimulation interface device, a neurostimulation signal or signal sequence to at least a subset of the afferent sensory neurons using the updated stimulation parameters
wherein the neurostimulation signal or signal sequence is configured to elicit an artificial sensory perception in a sensory cortex area receiving afferent sensory input from the stimulated subset of afferent sensory neurons.

16. The method of claim 1, wherein the device comprises a neurostimulation (NS) device or a computer-brain interface (CBI) device.

17. A non-transitory computer-readable memory medium storing program instructions which, when executed by a processor, cause a device to:
apply, via a neurostimulation interface device operably connected to the device, a burst sequence of stimulation pulses to a plurality of afferent sensory neurons of an individual targeting a sensory cortex area involved with decoding information transmitted by the device, wherein the sequence of stimulation pulses is associated with the current set of stimulation parameters, and wherein the sequence of stimulation pulses is configured to elicit a bioelectric response in the plurality of afferent sensory neurons;
record, via the neurostimulation interface device, the elicited bioelectric response of the stimulated afferent sensory neurons;
derive, based at least in part on the recorded bioelectric response, a neural excitability profile characterizing a non-linear, dynamic excitation behavior of the plurality of afferent sensory neurons corresponding to the applied sequence of stimulation pulses; and
adjust, based on the derived excitability profile, at least one stimulation parameter of the current set of stimulation parameters to obtain an updated set of stimulation parameters.

18. The non-transitory computer-readable memory medium of claim 17,
wherein the burst sequence of stimulation pulses is part of a neurostimulation signal or signal sequence applied by the device to elicit an artificial sensory perception in a sensory cortex area receiving input signals from at least a subset of the plurality of afferent sensory neurons,
wherein the burst sequence of stimulation pulses comprises a burst sequence of essentially identical pulses and/or phasic stimulation pulses; and
wherein an intra-burst pulse frequency is at least 50 Hz.

19. A device, comprising:
a processor;
a non-transitory computer-readable memory medium operably coupled to the processor; and
a neurostimulation interface device operably coupled to the processor, wherein the device is configured to:
apply, via the neurostimulation interface device, a burst sequence of stimulation pulses to a plurality of afferent sensory neurons of an individual targeting a sensory cortex area involved with decoding information transmitted by the device, wherein the sequence of stimulation pulses is associated with the current set of stimulation parameters, and wherein the sequence of stimulation pulses is configured to elicit a bioelectric response in the plurality of afferent sensory neurons;
record, via the neurostimulation interface device, the elicited bioelectric response of the stimulated afferent sensory neurons;
derive, based at least in part on the recorded bioelectric response, a neural excitability profile characterizing a non-linear, dynamic excitation behavior of the plurality of afferent sensory neurons corresponding to the applied sequence of stimulation pulses; and
adjust, based on the derived excitability profile, at least one stimulation parameter of the current set of stimulation parameters to obtain an updated set of stimulation parameters.

20. The device of claim 19,
wherein the device comprises:
a neurostimulation (NS) device; or
a computer brain interface (CBI) device.

* * * * *